(12) United States Patent
Rosenberg et al.

(10) Patent No.: US 11,045,629 B2
(45) Date of Patent: Jun. 29, 2021

(54) SYSTEM FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US); Kyle P. Taylor, Brooklyn Park, MN (US); Andrew T. Forsberg, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 216 days.

(21) Appl. No.: 16/422,638

(22) Filed: May 24, 2019

(65) Prior Publication Data

US 2019/0275298 A1 Sep. 12, 2019

Related U.S. Application Data

(60) Continuation of application No. 15/493,412, filed on Apr. 21, 2017, now Pat. No. 10,384,037, which is a
(Continued)

(51) Int. Cl.
*A61M 25/00* (2006.01)
*A61M 25/04* (2006.01)
*A61M 25/02* (2006.01)

(52) U.S. Cl.
CPC ............ *A61M 25/04* (2013.01); *A61M 25/02* (2013.01); *A61M 2025/028* (2013.01); *A61M 2025/0233* (2013.01); *A61M 2025/0286* (2013.01)

(58) Field of Classification Search
CPC .................. A61M 25/04; A61M 25/02; A61M 2025/028; A61M 2025/0286; A61M 2025/0246; A61B 2017/3484
See application file for complete search history.

(56) References Cited

U.S. PATENT DOCUMENTS

| 1,242,314 | A | 10/1917 | Bean |
| 1,380,447 | A | 6/1921 | Wescott |

(Continued)

FOREIGN PATENT DOCUMENTS

| EP | 0341039 | 11/1989 |
| WO | WO 1991015254 | 10/1991 |

(Continued)

OTHER PUBLICATIONS

Johnson & Johnson web page printout, "The EndoANCHOR Comparative Summary" printed Sep. 13, 2005, 2 pages.
(Continued)

*Primary Examiner* — William R Carpenter
(74) *Attorney, Agent, or Firm* — Fish & Richardson P.C.

(57) ABSTRACT

Some embodiments of a medical device anchor system include an anchor device that receives a catheter (or other medical instrument) and secures the catheter in place relative to a skin penetration point. In some embodiments, the anchor device can secure the catheter in an operative position relative to the skin without the use of sutures or skin tapes. In particular embodiments, the anchor device can be adjusted to a folded condition so that subcutaneous anchors are partially rotated prior to removal from the skin penetration point.

17 Claims, 11 Drawing Sheets

Related U.S. Application Data continuation of application No. 14/643,237, filed on Mar. 10, 2015, now Pat. No. 9,656,045, which is a continuation of application No. 13/677,825, filed on Nov. 15, 2012, now Pat. No. 8,986,257, which is a division of application No. 13/672,882, filed on Nov. 9, 2012, now Pat. No. 8,974,434, which is a division of application No. 12/367,164, filed on Feb. 6, 2009, now Pat. No. 8,328,764.

(56) References Cited

U.S. PATENT DOCUMENTS

| | | |
|---|---|---|
| 1,624,716 A | 4/1927 | Ferdinando |
| 1,998,225 A | 4/1935 | Frances |
| 2,525,398 A | 10/1950 | Collins |
| 3,039,468 A | 6/1962 | Price |
| 3,059,645 A | 10/1962 | Hasbrouck et al. |
| 3,108,595 A | 10/1963 | Overment |
| 3,176,690 A | 4/1965 | HDoubler |
| 3,308,819 A | 3/1967 | Arp |
| 3,630,195 A | 12/1971 | Santomieri |
| 3,677,250 A | 7/1972 | Thomas |
| 3,717,151 A | 2/1973 | Collett |
| 3,765,032 A | 10/1973 | Palma |
| 3,777,761 A | 12/1973 | Sheridan |
| 3,825,010 A | 7/1974 | McDonald |
| 3,834,380 A | 9/1974 | Boyd |
| 3,856,009 A | 12/1974 | Winnie |
| 3,896,527 A | 7/1975 | Miller et al. |
| 3,902,501 A | 9/1975 | Citron et al. |
| 3,938,529 A | 2/1976 | Gibbons |
| 4,043,346 A | 8/1977 | Mobley et al. |
| 4,083,370 A | 4/1978 | Taylor |
| 4,114,618 A | 9/1978 | Vargas |
| 4,164,943 A | 8/1979 | Hill et al. |
| 4,230,110 A | 10/1980 | Beroff |
| 4,248,224 A | 2/1981 | Jones |
| 4,278,092 A | 7/1981 | Borsanyi et al. |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,279 A | 1/1991 | O'Neill |
| 4,986,810 A | 1/1991 | Semrad |
| 5,041,085 A | 8/1991 | Osborne et al. |
| 5,067,957 A | 11/1991 | Jervis |
| 5,088,979 A | 2/1992 | Filipi et al. |
| 5,122,122 A | 6/1992 | Allgood |
| 5,190,546 A | 3/1993 | Jervis |
| 5,253,643 A | 10/1993 | Price |
| 5,256,146 A | 10/1993 | Ensminger et al. |
| 5,257,975 A | 11/1993 | Foshee |
| 5,267,960 A | 12/1993 | Hayman et al. |
| 5,279,564 A | 1/1994 | Taylor |
| 5,312,337 A | 5/1994 | Flaherty et al. |
| 5,330,501 A * | 7/1994 | Tovey ............... A61B 17/3421 604/105 |
| 5,344,439 A | 9/1994 | Otten |
| 5,353,787 A | 10/1994 | Price |
| 5,354,279 A | 10/1994 | Hofling |
| 5,368,017 A | 11/1994 | Sorenson et al. |
| 5,377,667 A | 1/1995 | Patton et al. |
| 5,378,239 A | 1/1995 | Termin et al. |
| 5,391,156 A | 2/1995 | Hildwein et al. |
| 5,419,777 A | 5/1995 | Hofling |
| 5,456,671 A | 10/1995 | Bierman |
| 5,470,321 A | 11/1995 | Forster et al. |
| 5,496,277 A | 3/1996 | Termin et al. |
| 5,531,676 A | 7/1996 | Edwards et al. |
| 5,540,648 A | 7/1996 | Yoon |
| 5,578,013 A | 11/1996 | Bierman |
| 5,597,378 A | 1/1997 | Jervis |
| 5,599,311 A | 2/1997 | Raulerson |
| 5,616,131 A | 4/1997 | Sauer et al. |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,792,115 A | 8/1998 | Horn |
| 5,800,402 A | 9/1998 | Bierman |
| 5,810,781 A | 9/1998 | Bierman |
| 5,814,065 A | 9/1998 | Diaz |
| 5,817,062 A | 10/1998 | Flom et al. |
| 5,827,230 A | 10/1998 | Bierman |
| 5,833,664 A | 11/1998 | Seare |
| 5,833,667 A | 11/1998 | Bierman |
| 5,857,999 A | 1/1999 | Quick et al. |
| 5,879,333 A | 3/1999 | Smith |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,984,896 A | 11/1999 | Boyd |
| 5,989,265 A | 11/1999 | Bouquet De La Joliniere et al. |
| 6,090,072 A | 7/2000 | Kratoska et al. |
| 6,213,979 B1 | 4/2001 | Bierman |
| 6,217,527 B1 | 4/2001 | Selmon et al. |
| 6,217,554 B1 | 4/2001 | Green |
| 6,231,548 B1 | 5/2001 | Bassett |
| 6,290,676 B1 | 9/2001 | Bierman |
| 6,413,240 B1 | 7/2002 | Bierman et al. |
| 6,447,485 B2 | 9/2002 | Bierman |
| 6,533,762 B2 | 3/2003 | Kanner et al. |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,638,234 B2 | 10/2003 | Burbank et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,786,892 B2 | 9/2004 | Bierman |
| 6,827,705 B2 | 12/2004 | Bierman |
| 6,837,875 B1 | 1/2005 | Bierman et al. |
| 6,896,665 B2 | 5/2005 | Picha et al. |
| 6,929,625 B2 | 8/2005 | Bierman |
| 6,958,044 B2 | 10/2005 | Burbank et al. |
| 6,972,003 B2 | 12/2005 | Bierman et al. |
| 7,018,362 B2 | 3/2006 | Bierman et al. |
| 7,056,286 B2 | 6/2006 | Ravenscroft et al. |
| 7,087,069 B2 | 8/2006 | Petrovic et al. |
| 7,247,150 B2 | 7/2007 | Bierman |
| 7,273,468 B2 | 9/2007 | Bedell |
| 7,377,910 B2 | 5/2008 | Katoh et al. |
| 7,753,889 B2 | 7/2010 | Rosenberg |
| 7,811,251 B2 | 10/2010 | Wenchell et al. |
| 7,931,658 B2 | 4/2011 | Rosenberg et al. |
| 7,935,127 B2 | 5/2011 | Rosenberg et al. |
| 8,016,794 B2 | 9/2011 | Rosenberg et al. |
| 8,016,813 B2 | 9/2011 | Rosenberg et al. |
| 8,029,476 B2 * | 10/2011 | Rosenberg ............ A61M 25/02 604/174 |
| 8,038,653 B2 | 10/2011 | Rosenberg et al. |
| 8,137,323 B2 | 3/2012 | Rosenberg |
| 8,142,401 B2 | 3/2012 | Rosenberg |
| 8,147,459 B2 | 4/2012 | Rosenberg |
| 8,235,948 B2 | 8/2012 | Rosenberg et al. |
| 8,252,004 B2 | 8/2012 | Rosenberg et al. |

(56) References Cited

U.S. PATENT DOCUMENTS

| | | | |
|---|---|---|---|
| 8,328,764 B2 * | 12/2012 | Rosenberg | A61M 25/04 604/175 |
| 8,394,066 B2 | 3/2013 | Rosenberg | |
| 8,444,603 B2 | 5/2013 | Rosenberg et al. | |
| 8,579,864 B2 | 11/2013 | Rosenberg et al. | |
| 8,585,654 B2 | 11/2013 | Rosenberg | |
| 8,628,511 B2 | 1/2014 | Rosenberg | |
| 8,715,295 B2 | 5/2014 | Rosenberg | |
| 8,771,232 B2 | 7/2014 | Rosenberg et al. | |
| 8,920,380 B2 | 12/2014 | Rosenberg | |
| 8,936,576 B2 | 1/2015 | Rosenberg | |
| 8,956,329 B2 | 2/2015 | Rosenberg | |
| 8,974,434 B2 | 3/2015 | Rosenberg et al. | |
| 8,986,257 B2 | 3/2015 | Rosenberg et al. | |
| 9,056,187 B2 | 6/2015 | Rosenberg et al. | |
| 9,205,230 B2 | 12/2015 | Rosenberg | |
| 9,227,040 B2 | 1/2016 | Rosenberg et al. | |
| 9,283,355 B2 | 3/2016 | Rosenberg | |
| 9,314,596 B2 | 4/2016 | Rosenberg | |
| 9,381,321 B2 | 7/2016 | Rosenberg | |
| 9,381,322 B2 | 7/2016 | Rosenberg | |
| 9,545,503 B2 | 1/2017 | Rosenberg | |
| 9,656,045 B2 | 5/2017 | Rosenberg et al. | |
| 9,884,168 B2 | 2/2018 | Rosenberg | |
| 9,937,327 B2 * | 4/2018 | Rosenberg | A61M 25/02 |
| 10,335,576 B2 | 7/2019 | Rosenberg | |
| 2001/0056261 A1 | 12/2001 | Lerman et al. | |
| 2002/0068898 A1 | 6/2002 | McGucklin, Jr. et al. | |
| 2002/0068899 A1 | 6/2002 | McGucklin, Jr. et al. | |
| 2002/0120250 A1 | 8/2002 | Altman | |
| 2002/0165489 A1 | 11/2002 | McGucklin, Jr. et al. | |
| 2003/0040712 A1 | 2/2003 | Ray et al. | |
| 2004/0098047 A1 * | 5/2004 | Frazier | A61B 17/00234 606/222 |
| 2004/0176726 A1 | 9/2004 | Katoh et al. | |
| 2005/0043685 A1 | 2/2005 | Schinkel-Fleitmann | |
| 2005/0137498 A1 | 6/2005 | Sakal et al. | |
| 2005/0177105 A1 | 8/2005 | Shalev | |
| 2005/0256458 A1 | 11/2005 | Howard et al. | |
| 2005/0256459 A1 | 11/2005 | Howard et al. | |
| 2005/0273058 A1 | 12/2005 | Bierman | |
| 2006/0079845 A1 | 4/2006 | Howard et al. | |
| 2007/0021685 A1 | 1/2007 | Oepen et al. | |
| 2007/0078397 A1 | 4/2007 | Weststrate | |
| 2007/0106330 A1 | 5/2007 | Rosenberg | |
| 2007/0225651 A1 | 9/2007 | Rosenberg et al. | |
| 2007/0232997 A1 | 10/2007 | Glenn | |
| 2008/0312599 A1 | 12/2008 | Rosenberg | |
| 2009/0054843 A1 | 2/2009 | Lundqvist | |
| 2009/0099527 A1 | 4/2009 | Rosenberg et al. | |
| 2009/0326470 A1 | 12/2009 | Rosenberg | |
| 2009/0326473 A1 | 12/2009 | Rosenberg et al. | |
| 2010/0016801 A1 | 1/2010 | Rosenberg et al. | |
| 2010/0204656 A1 | 8/2010 | Rosenberg et al. | |
| 2010/0241084 A1 | 9/2010 | Rosenberg | |
| 2011/0172607 A1 | 7/2011 | Rosenberg | |
| 2011/0301543 A1 | 12/2011 | Rosenberg et al. | |
| 2012/0004617 A1 | 1/2012 | Rosenberg et al. | |
| 2012/0004618 A1 | 1/2012 | Rosenberg | |
| 2012/0157925 A1 | 6/2012 | Rosenberg | |
| 2012/0157926 A1 | 6/2012 | Rosenberg | |
| 2012/0157927 A1 | 6/2012 | Rosenberg | |
| 2012/0271238 A1 | 10/2012 | Rosenberg | |
| 2012/0283644 A1 | 11/2012 | Rosenberg | |
| 2013/0066277 A1 | 3/2013 | Rosenberg et al. | |
| 2013/0072875 A1 | 3/2013 | Rosenberg | |
| 2013/0072877 A1 | 3/2013 | Rosenberg | |
| 2013/0096506 A1 | 4/2013 | Rosenberg | |
| 2013/0131599 A1 | 5/2013 | Rosenberg | |
| 2013/0190727 A1 | 7/2013 | Rosenberg | |
| 2014/0046264 A1 | 2/2014 | Rosenberg et al. | |
| 2014/0058331 A1 | 2/2014 | Rosenberg | |
| 2014/0107583 A1 | 4/2014 | Rosenberg | |
| 2014/0107584 A1 | 4/2014 | Rosenberg | |
| 2014/0207147 A1 | 7/2014 | Rosenberg | |
| 2014/0276438 A1 | 9/2014 | Rosenberg | |
| 2014/0330247 A1 | 11/2014 | Rosenberg | |
| 2015/0080804 A1 | 3/2015 | Rosenberg | |
| 2015/0133867 A1 | 5/2015 | Rosenberg | |
| 2015/0174373 A1 | 6/2015 | Rosenberg | |
| 2015/0246208 A1 | 9/2015 | Rosenberg | |
| 2016/0151609 A1 | 6/2016 | Rosenberg | |
| 2016/0279389 A1 | 9/2016 | Rosenberg | |
| 2017/0120007 A1 | 5/2017 | Rosenberg | |
| 2018/0161545 A1 | 6/2018 | Rosenberg | |
| 2018/0207405 A1 | 7/2018 | Rosenberg et al. | |

FOREIGN PATENT DOCUMENTS

| | | |
|---|---|---|
| WO | WO 2004026152 | 4/2004 |
| WO | WO 2005039419 | 5/2005 |
| WO | WO 2005102438 | 11/2005 |
| WO | WO 2007082333 | 7/2007 |
| WO | WO 2007103999 | 9/2007 |
| WO | WO 2008051810 | 5/2008 |

OTHER PUBLICATIONS

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Web Page Printout of Statlock Device, 2 pages.

* cited by examiner

SYSTEM FOR ANCHORING MEDICAL DEVICES

CROSS-REFERENCE TO RELATED APPLICATION(S)

This is a continuation of U.S. patent application Ser. No. 15/493,412 filed on Apr. 21, 2017, which is a continuation of U.S. patent application Ser. No. 14/643,237 filed on Mar. 10, 2015 (now U.S. Pat. No. 9,656,045 issued May 23, 2017), which is a continuation of U.S. patent application Ser. No. 13/677,825 filed on Nov. 15, 2012 by Rosenberg et al. (now U.S. Pat. No. 8,986,257 issued Mar. 24, 2015), which is a division of U.S. patent application Ser. No. 13/672,882 filed on Nov. 9, 2012 by Rosenberg et al. (now U.S. Pat. No. 8,974,434 issued Mar. 10, 2015), which is a division of U.S. patent application Ser. No. 12/367,164 filed on Feb. 6, 2009 by Rosenberg et al. (now U.S. Pat. No. 8,328,764 issued Dec. 11, 2012). The entire contents of these previous applications are incorporated herein by reference.

TECHNICAL FIELD

This document relates to an anchor device, such as a device for use in securing the position of a catheter or another medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In conventional practice, the catheter is commonly secured to the patient using an adhesive tape on the skin or by suturing a catheter hub to the patient's skin.

SUMMARY

Some embodiments of a medical device anchor system include an anchor device that receives a medical instrument (such as a catheter or the like) and secures the instrument in place relative to a skin penetration point. In some circumstances, the anchor device can be actuated so that subcutaneous anchors are inserted through the skin penetration point that is already occupied by the medical instrument. Such a configuration may allow the anchor device to be used after medical instrument is already in place without the need for a second penetration point for the anchor device. In particular embodiments, the anchor device may have a pivoting design for the subcutaneous anchors so as to facilitate removal of the device and reduce trauma to surrounding tissue near the penetration point. For example, the anchor device can be adjusted to a folded condition so that the subcutaneous anchors are partially rotated prior to removal from the skin penetration point. In these circumstances, the subcutaneous anchors can be contemporaneously removed from the skin penetration point with an upward withdrawal force in a manner that reduces the likelihood of damage to the tissue surrounding the skin penetration point.

In some embodiments, an anchor device for securing the position of a catheter can include a retainer body to releasably couple to the catheter. The retainer body may include a first body portion that is pivotably coupled to a second body portion. The anchor device may also include first and second anchors that extend distally from the retainer body. Each anchor may include a flexible tine that is deployable in a subcutaneous region to secure the retainer body relative to a penetration point. The first anchor may be coupled to the first body portion and the second anchor being coupled to the second body portion. The first body portion of the retainer body may be pivotable relative to the second body portion so that the first and second anchors are adjustable from a deployed configuration in which the flexible tines extend generally away from one another to a removal configuration in which the flexible tines extend generally in the same direction.

In further embodiments, an anchor system for securing the position of a medical instrument can include a delivery device and an anchor device. The delivery device can advance the anchor device toward a skin penetration point that is occupied by the medical instrument. The delivery device may define an internal space and a distal opening. The anchor device may be deployable from the internal space of the delivery device. Also, the anchor device may comprise a retainer base to releasably secure with the medical instrument. The anchor device may further comprise one or more subcutaneous anchors that extend distally from the retainer base and toward the skin penetration point when the delivery device deploys the one or more subcutaneous anchors from the distal opening. Each anchor may include a tine that deploys in a subcutaneous region to secure the retainer base relative to the skin penetration point. Also, each tine may be pivotable about a longitudinal axis from a deployed configuration to a removal configuration.

Some embodiments of a method of using a catheter anchor device may include advancing a catheter though a skin penetration point and directing an anchor device toward the skin penetration point that is occupied by a portion of the catheter. The anchor device may comprise a retainer body to releasably couple to an external portion of the catheter arranged outside the body, and first and second anchors that extend distally from the retainer body. The method may further include inserting the first and second anchors through the skin penetration point that is occupied by the catheter so that at least a portion of the first and second anchors are deployed in a subcutaneous region proximate the skin penetration point. The method may also include securing the catheter with the retainer body so that the catheter is anchored relative to the skin penetration point. The method may further include pivoting the first and second anchors about a longitudinal fold line defined by the retainer body so that the first and second anchors are adjusted from a deployed configuration to a removal configuration. The method may also include removing the first and second anchors from the subcutaneous region and the skin penetration point.

These and other embodiments may provide one or more of the following advantages. First, some embodiments of an anchor system can retain a medical instrument in a desired position relative to a skin penetration point without necessarily requiring sutures or skin adhesives. Second, in some embodiments, an anchor device can include a retention portion that readily mates with a medical instrument (such as a catheter) and at least one anchor extending distally from the retention portion to engage the skin penetration point as the medical instrument. Third, the anchor device can include one or more anchors configured to deploy in a subcutaneous region under the skin proximate to the skin penetration point of the medical instrument. In such circumstances, the anchors may be inserted through the skin penetration point in a manner that reduces the likelihood of trauma to the surround skin tissue. Fourth, in some embodiments, the anchor device may be partially folded or otherwise adjusted so that the subcutaneous anchors are partially rotated prior to removal from the skin penetration point. For example, the subcutaneous anchors may include tines that extend outwardly away from one another when deployed in the subcutaneous region, but can be partially rotated to extend in a generally side-by-side orientation during removal from the skin. In these circumstances, the subcutaneous anchors may be readily removed from the skin penetration point with a noncomplex upward force. Fifth, some embodiments of the anchor device may include a delivery device that facilitates delivery of the anchors toward the skin penetration point. For example, the delivery device may be configured as a disposable, hand-held actuator that provides for convenient grasping by a user. Moreover, the delivery device can be actuated so as to deploy the anchors into the subcutaneous region before the delivery device is removed from the anchor device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
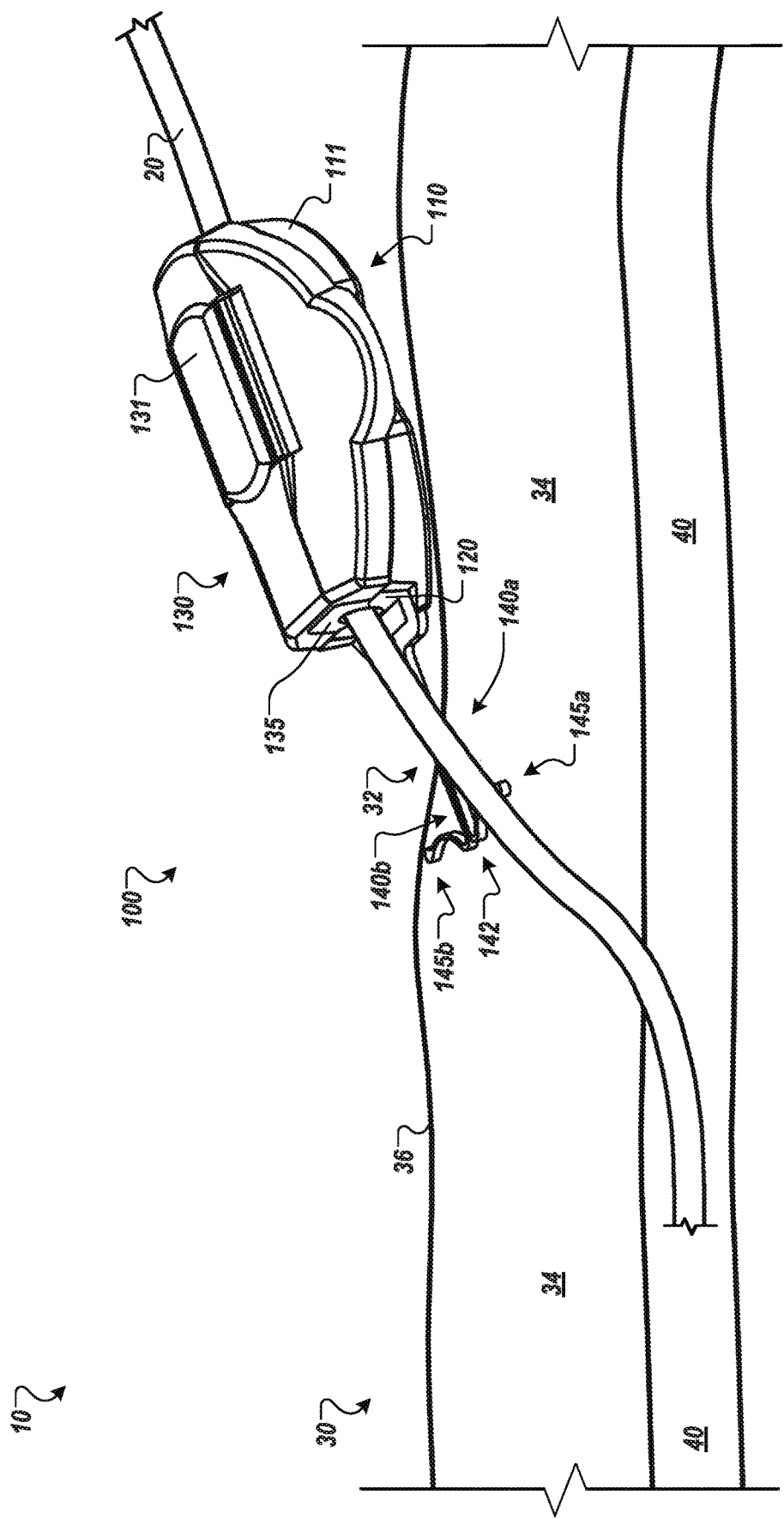
FIG. 1 is a perspective view of an anchor device with a portion of the device located in a subcutaneous region, in accordance with some embodiments.

Referring to FIG. 1, some embodiments of a medical device anchor system 10 include an anchor device 100 that releasably retains a medical instrument 20 (e.g., depicted as a catheter in this embodiment) in an operative position relative to a portion of skin 30 (e.g., relative to a skin penetration point 32). The anchor device 100 may include a base 110 and a cap assembly 130. The base 110 may include a retainer body 111 and one or more anchors 140a-b that extend distally from the retainer body 111 for deployment in a subcutaneous layer 34. The base 110 can receive the medical instrument 20, and the cap assembly 130 can be removably coupled to the base 110 to secure the medical instrument 20 in a generally fixed position relative to the base 110. As described in greater detail below in connection with FIGS. 2-3, the base 110 and the cap assembly 130 can include gripping members 120 and 135, respectively. When the cap assembly 130 is coupled to the base 110, the gripping members 120 and 135 can releasably engage with an outer surface of the medical instrument 20. The medical instrument 20 can extend from the gripping members 120 and 135 and through a penetration point 32 in a patient's skin 30 (e.g., through a small incision, a puncture, or the like), while the retainer body 111 and the gripping members 120 and 135 remain outside of the skin 30.

As described in more detail below, the anchor device 100 can secure the catheter 20 in the operative position relative to the penetration point 32 without necessarily requiring sutures or adhesive tapes bonded to the skin. For example, the base 110 can include the one or more anchors 140a and 140b that extend distally from the retainer body 111 so as to penetrate through the same skin opening as the medical instrument 20. The anchors 140a and 140b can include tines 145a and 145b that, after insertion, reside in the subcutaneous region 34 (e.g., a region under the dermal layers of the skin 30 that may comprise a fatty tissue layer) so as to secure the position of the anchor device 100—and the medical instrument 20 retained therein—relative to the penetration point 32.

Figure 2:
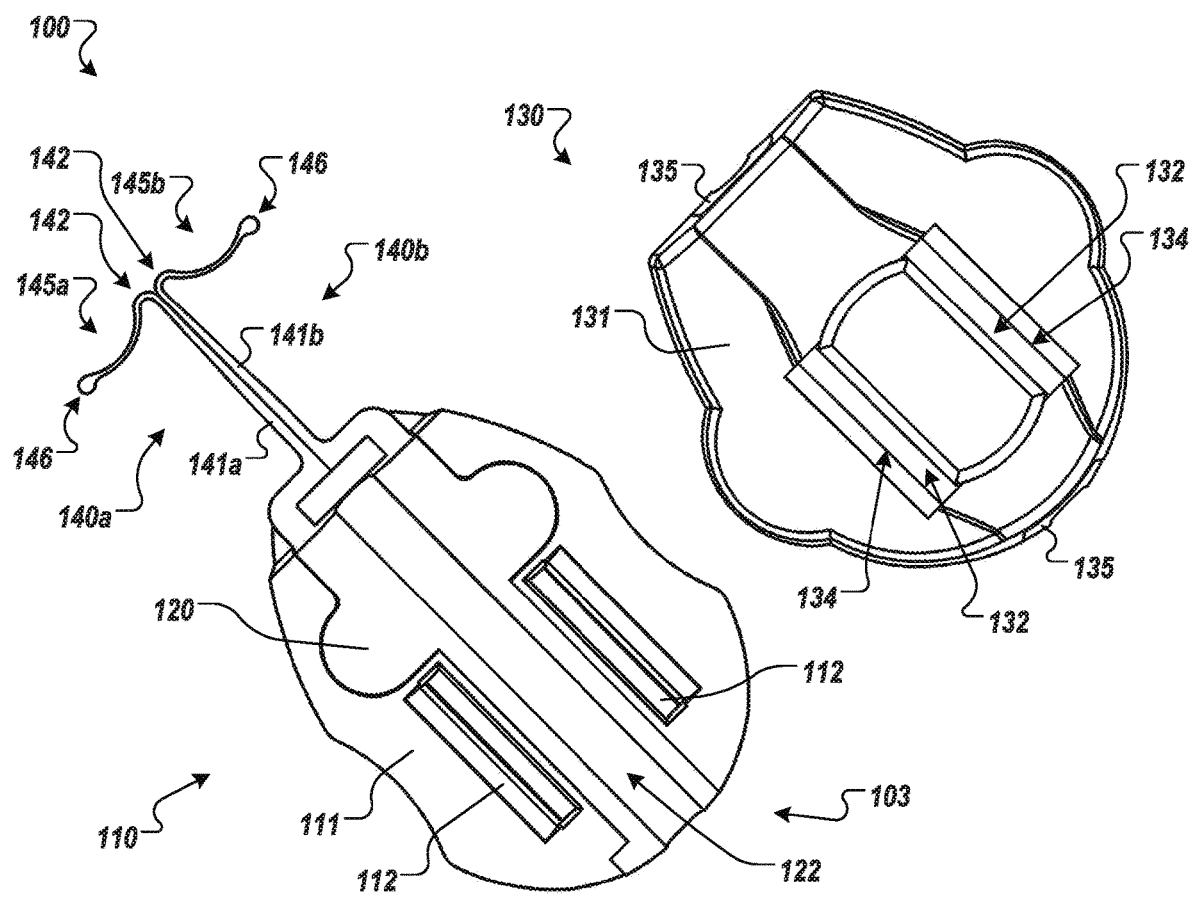
FIGS. 2-3 are top and front views, respectively, of the anchor device of FIG. 1 with the medical device retention portion in an open and deployed configuration.
Figure 3:
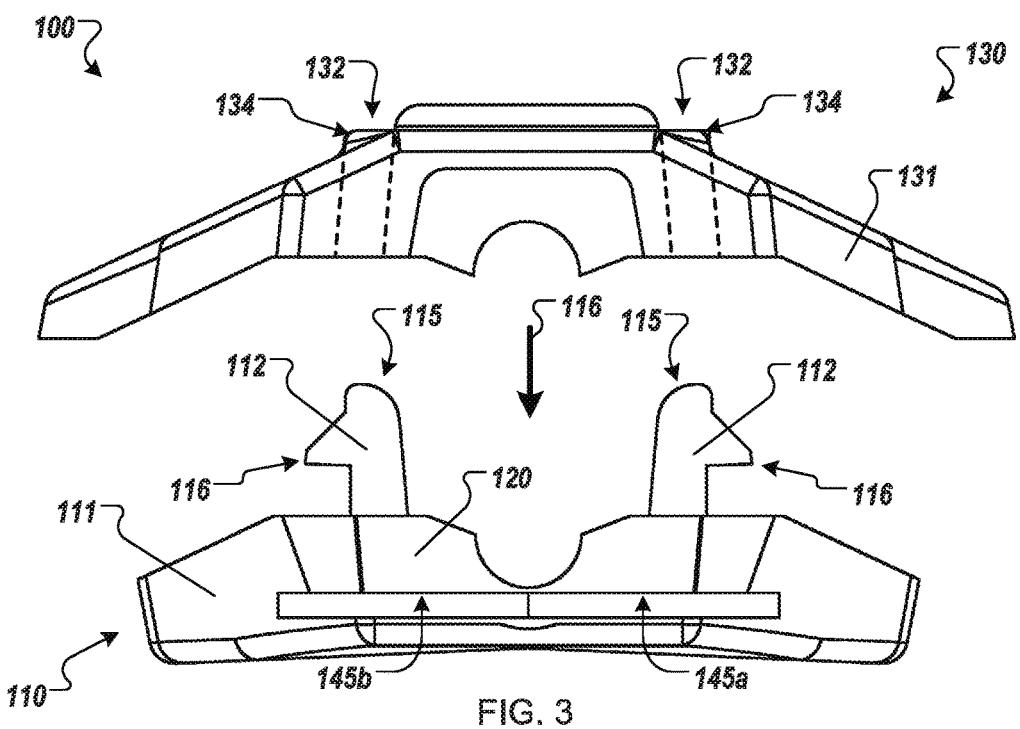

Referring now to FIGS. 1-3, in some embodiments, the medical instrument 20 can include a catheter to be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient. After placement of the catheter 20, the base 110 of the anchor device 100 can approach the penetration point 32 such that the tips 142 of the anchors 140a and 140b enter the skin 30 through the penetration point 32. As the anchor device 100 is inserted through the penetration point 32, the tines 145a and 145b are stressed to flex against anchor shafts 141a and 141b (refer also to FIG. 10) so as to pass through the penetration point 32 in a manner that reduces the likelihood of trauma to the surrounding skin tissue. As the anchors 140a and 140b are collectively advanced through the penetration point 32, the tines 145a and 145b are moved beneath the dermal skin layers 36 of the skin 30. When the tines 145a and 145b reach the subcutaneous region 34, the tines 145a and 145b are biased to return toward an unstressed shape, as shown in FIG. 2, thereby deploying in the subcutaneous region 34.

Referring now to FIG. 2, the anchors 140a and 140b may be designed such that the tines 145a and 145b include a curvature that abuts against the underside of the dermal layers 36 in a manner that reduces the likelihood of the tine tips 146 puncturing the underside of the dermal layers 36. When the tines 145a and 145b of the anchors 140a and 140b are deployed in the subcutaneous region 34, the cap assembly 130 can be removably coupled to the base 110 (see FIGS. 4A-4B), compressing the securing portions 120 and 135 of the anchor body 100 causing the securing portions 120 and 135 to releasably engage with an outer surface of the medical instrument 20. In this way, the anchor device 100 can be secured to the patient without the retainer body 111 penetrating though the skin 30 of the patient and without necessarily requiring sutures or adhesive tapes bonded to the skin 30.

In some embodiments, some of which are described in more detail below in connection with FIGS. 8A-8C and 9-13, a delivery tool 150 that can be used to deploy at least a portion of the anchor device 100 in the subcutaneous region 34 and can include features that advantageously cause the tines 145a and 145b to flex against anchor shafts 141a and 141b (refer to FIG. 10) until the tines 145a and 145b have passed through the penetration point 32, thereby reducing trauma to the surrounding skin tissue.

Referring now to FIGS. 2-3 and 4A-4B, some embodiments of the anchor device 100 can include structures designed to mate with portions of the medical instrument 20 to be retained by the anchor device 100. The anchor device 100 can include the gripping members 120 and 135 used to secure the catheter 20 (or other medical instrument) relative to the skin penetration point 32. For example, after the catheter 20 is delivered into the targeted vein 40 (or other bodily lumen) and after the tines 145a and 145b are deployed in the subcutaneous region 34, the cap assembly 130 can be removably coupled to the base 110, compressing the gripping members 120 and 135 to temporarily engage with the outer surface of the catheter 20. In this way, the anchor device 100 can be transitioned from the open configuration (shown in FIGS. 2-3) to the closed configuration (shown in FIGS. 4A-4B) to thereby secure the catheter 20 with the gripping members 120 and 135. As described in more detail below, the retainer body 111 can include locking tabs 112 that can pass through openings 132 in the cap 131 and positively engage at least a portion of perimeters 134 of the openings 132, thereby removably coupling the cap assembly 130 to the base 110.

Still referring to FIGS. 2-3 and 4A-B, the anchor device 100 can include features that facilitate separation from the catheter 20, which can permit the catheter 20 and anchor device 100 to be removed from the skin 30 independently of each other. For example, the tabs 112 may be disengaged from the cap assembly 130 to decouple the cap assembly 130 from the base 110. Once the cap assembly 130 is removed, the gripping members 120 and 135 can release from the catheter 20, thereby allowing the catheter 20 to be moved relative to the anchor device 100. As such, the catheter 20 can be moved independently from the anchor device 100, for example, to withdraw the catheter 20 from the patient while at least a portion of the anchor device 100 remains secured to the skin 30.

Figure 4A:
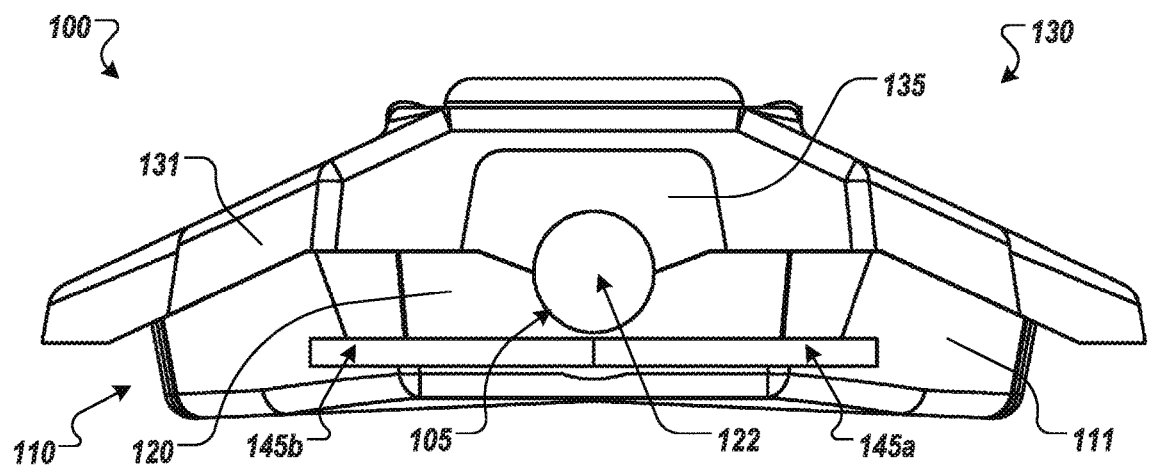
FIGS. 4A-4B are front and rear views, respectively, of the anchor device of FIG. 1 with the medical device retention portion in a closed and deployed configuration.
Figure 4B:
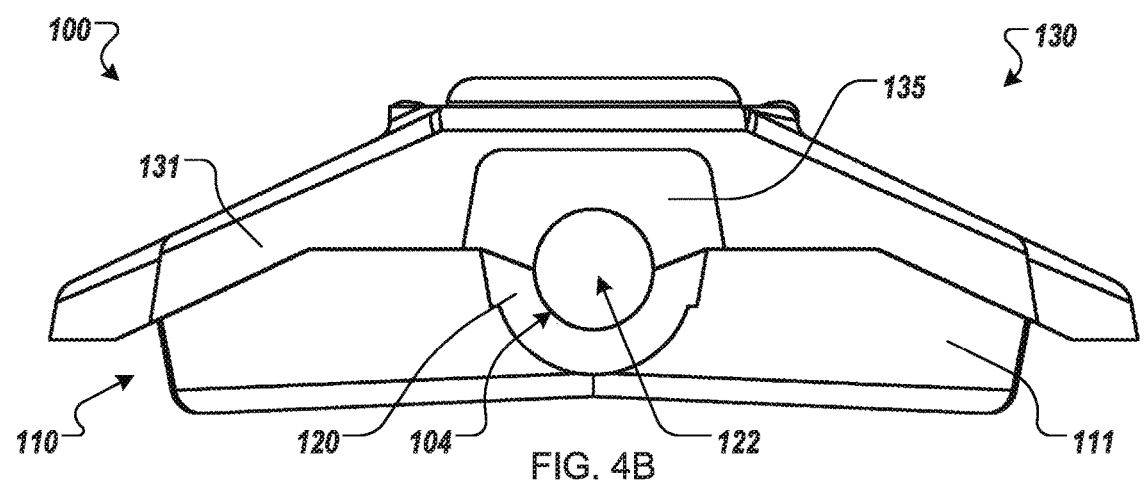

Some embodiments of the anchor device 100 can include structures configured to mate with portions of the medical instrument 20 to be retained by the anchor device 100. For example, when the anchor device is in the closed configuration (as depicted in FIGS. 4A-4B), the gripping members 120 and 135 can define a channel 122 that extends longitudinally from the proximal portion 103 of the anchor device 100 toward the anchors 140a and 140b. The channel 122 can be configured to complement an outer surface of the catheter 20 or other medical instrument to be anchored by the device 100. For example, during installation of the anchor device 100, the anchors 140a and 140b are directed toward the penetration point 32 through which the catheter 20 passes. When the tines 145a and 145b are deployed in the subcutaneous region 34, the cap assembly 130 can be removably coupled to the base 110, which transitions the anchor device 100 to the closed configuration. As shown in FIGS. 4A-4B, openings 104 and 105 can be defined by the base 110 and the cap assembly 130 when arranged in the closed configuration. As such, the catheter 20 can extend though the channel 122 when the anchors 140a and 140b are deployed under the skin 30.

In some embodiments, the anchor device 100 can be transitioned from the open configuration (FIGS. 2-3) to the closed configuration (FIGS. 4A-4B) when the cap assembly 130 is coupled to the base 110. For example, during installation, the base 110 can be guided so that the anchors 140a and 140b are directed through the penetration point 32 through which the catheter 20 passes. When the tines 145a and 145b are located in the subcutaneous region 34 securing the anchor device 100 relative to the skin 30 (see FIG. 1), the cap assembly 130 can be removably coupled to the base 110 to secure the catheter 20 relative to the anchor device 100, thus securing the catheter 20 relative to the skin 30. In some embodiments, features of the anchor device 100 can removably couple the base 110 to the cap assembly 130. In the example depicted in FIG. 3, the cap assembly 130 can be moved toward the base 110 (e.g., in the direction depicted by arrow 106) to direct the tabs 112 toward to the openings 132. When the diagonal faces of the tabs 112 contact the perimeters 134, the tabs 112 are stressed such that the tips 115 of the tabs 112 move closer to each other. When the face 135 moves beyond the engagement fingers 116, the tabs 112 can outwardly toward their unstressed positions to releasably engage the perimeters 134. When in this closed configuration, the cap assembly 130 and base 110 can apply a compressive force from the gripping members 120 and 135 to the catheter 20 in the channel 122, thereby applying a frictional holding force to the catheter 20 or medical instrument therein.

In some embodiments, the holding force that secures the catheter 20 to the anchor device 100 can be released by separating the cap assembly 130 from the base 110. The cap assembly 130 can be separated from the base 110 by disengaging the locking tabs 112 from the cap assembly 130. For example, the base 110 can be separated from the cap assembly 130 by applying pressure to the locking tabs 112 to move the tips 115 closer to each other. When the engagement portions 116 of the tabs 112 move inside the openings 132 in the cap 131, the retainer portions 120 and 135 force the cap assembly 130 away from the base 110 and the cap assembly 130 becomes decoupled from the base 110, thus transitioning the anchor device 100 to the open configuration (FIGS. 2-3). When the anchor device is in the open configuration, the catheter 20 can be moved relative to the anchor device 100.

Figure 5:
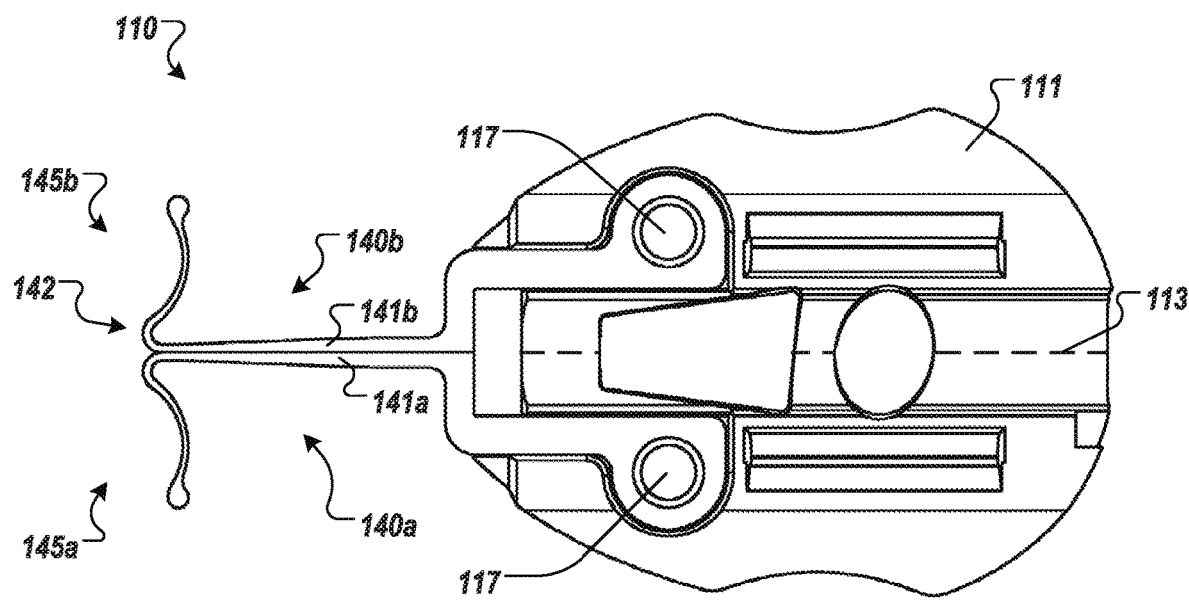
FIG. 5 is a top view of the anchor device of FIG. 1, with the medical retention portion removed view.

Referring now to FIG. 5 (which depicts the base 110 without the first gripping member 120), some embodiments of the base 110 can include features that facilitate assembly of the anchors 140a and 140b to the retainer body 111. The anchors 140a and 140b can be coupled to the retainer body 111 via one or more posts 117 in the retainer body 111 and corresponding openings 143 in the anchors 140a and 140b. For example, during manufacturing, the anchors 140a and 140b can be located such that the posts 117 occupy the openings 143, and an overmolding process can be used to secure the anchors 140a and 140b relative to the retainer body 111.

Figure 10:
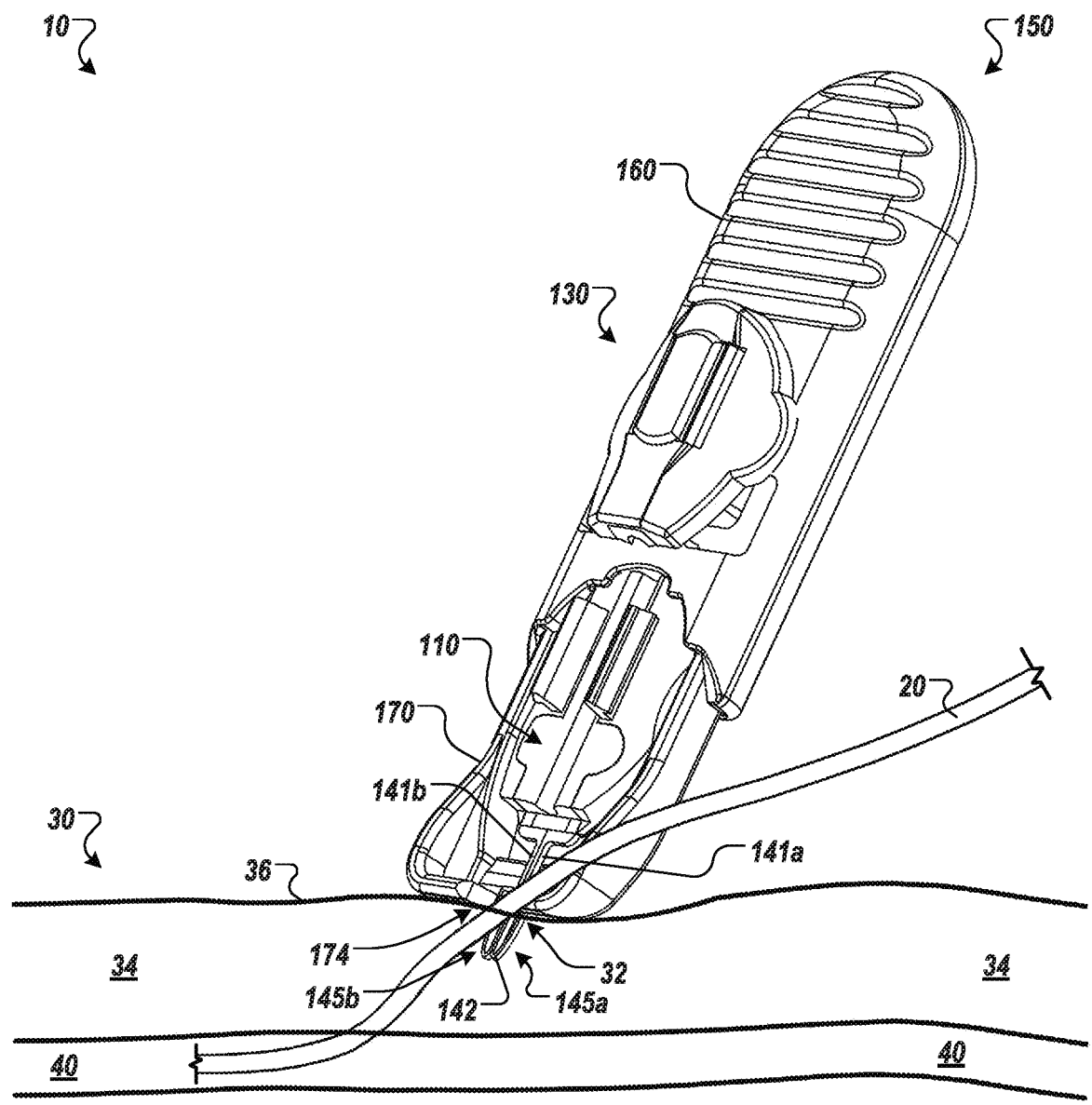

The anchors 140a and 140b may comprise a material that exhibits superelasticity when used in a patient's body. When the tines 145a and 145b of anchors 140a and 140b are stressed by insertion through the skin penetration point 32, the tines 145a and 145b can superelastically flex from an expanded position (see FIG. 2) to a partially contracted position (see FIG. 10). In this partially contracted position, at least a portion of the tines 145a and 145b may flex against the anchor shafts 141a and 141b. While against the anchor shafts 141a and 141b, the tines 145a and 145b can readily penetrate through the skin penetration point 32 (which may be generally smaller in width than the width occupied by the tines 145a and 145b in a fully expanded state). Such a feature can reduce the damage to the patient's skin 30 during deployment of the anchors 140a and 140b. In another example, as described in more detail below in connection with FIGS. 8A-8C, features of the anchor device 100 can cooperate with corresponding features in the delivery tool 150 so as to minimize the likelihood of damage to surrounding tissue when the anchors 140a and 140b are deployed into the subcutaneous region 34. As depicted in FIG. 10, the delivery tool 150 can minimize damage by holding at least a portion of the tines 145a and 145b against the anchor shafts 141 and 141b as the anchors 140a and 140b pass through the skin penetration point 32.

In some embodiments, at least a portion of the anchors 140a and 140b (including the tines 145a and 145b) may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), or the like. Alternatively, the anchors 140a and 140b may comprise a metal material such as stainless steel (e.g., 304 stainless, 316 stainless, custom 465 stainless, and the like), spring steel, titanium, MP35N, and other cobalt alloys, or the like. In another alternative, the anchors 140a and 140b may be formed from a resilient polymer material. In some embodiments, the anchors 140a and 140b can be formed from a material or materials that allow the tines 145a and 145b to be flexed to a contracted position (e.g., as in FIG. 10) and can resiliently return to an expanded position (e.g., as in FIG. 5).

Figure 6:
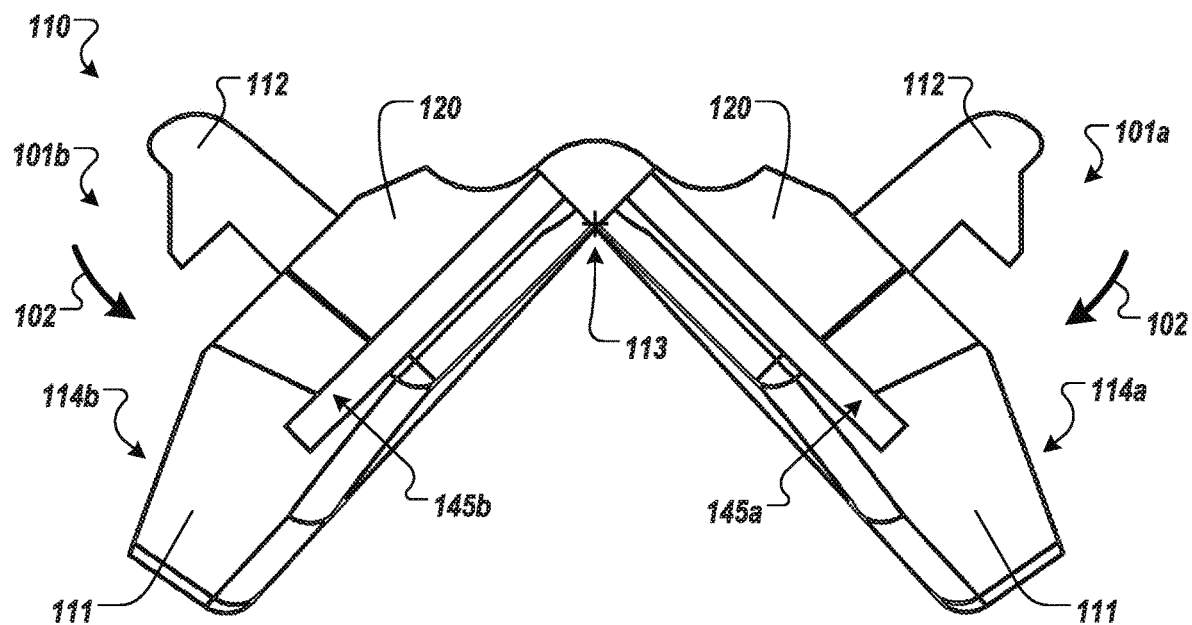
FIG. 6 depicts a front view of the anchor device of FIG. 1 with the anchor device in a transitional configuration between a deployed configuration and removal configuration.
Figure 7:
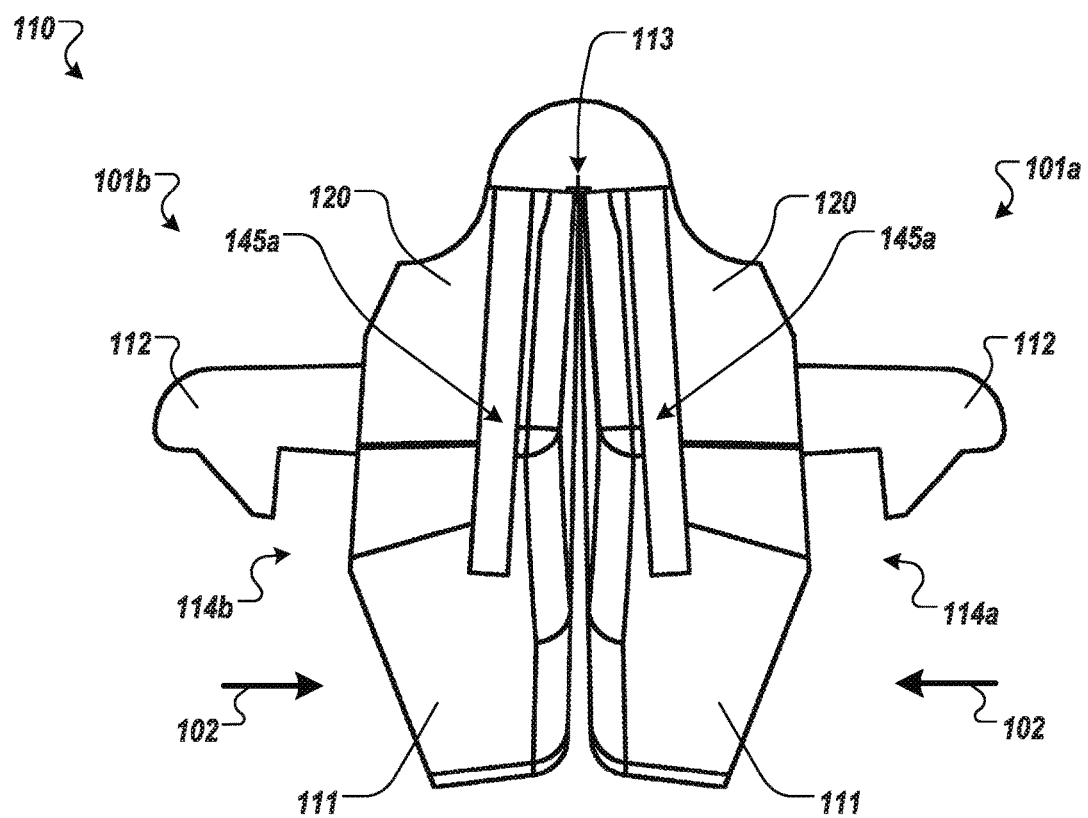
FIG. 7 depicts a front view of the anchor device of FIG. 1 with the anchor device in a removal configuration.

Referring now to FIGS. 5-7, the anchor device 100 can include features that allow the individual anchors 140a and 140b to be moved relative to each other so as to facilitate removal of the anchor device 100 from the skin 30. In some embodiments, the anchor device 100 comprises a foldable design in which a first portion of the base 110 is pivotably coupled to a second portion of the base 110. For example, the anchor device 100 can include a left portion 101a and a right portion 101b (refer to FIGS. 6-7), which can be flexibly pivoted with respect to each other along a fold line 113 extending longitudinally through the retainer body 111. The left portion 101a can include a left retainer body portion 114a fixedly coupled to the anchor 140a, and the right portion 101b can include a right retainer body portion 114b fixedly coupled to the anchor 140b. Thus, when the left and right retainer body portions 114a and 114b are pivoted about the fold line 113, the two anchors 140a and 140b likewise pivot relative to one another. This process of folding the anchor device 100 can cause the anchor device 100 to transition from a deployed configuration (shown in FIG. 2) where the tines 145a and 145b are oriented to extend in opposing directions, through an intermediate configuration (shown in FIG. 6), and to a removal configuration (shown in FIG. 7) where the tines 145a and 145b are generally adjacent to each other and oriented to extend in substantially the same direction. As described in more detail below in connection with FIGS. 14-15, folding the anchor device 100 into the removal configuration permits the anchors 140a and 140b to be maneuvered in a manner that reduces the likelihood of the tines 145a and 145b causing damage to the skin 30 during removal.

The left and right retainer body portions 114a and 114b can comprise a biocompatible polymer material (e.g., PVC, polypropylene, polystyrene, or the like). In such embodiments, the retainer body 111 can be formed using a molding process in which the retainer body 111 is overmolded around a portion of the anchors 140a and 140b. For example, the anchor 140a can include the opening 143. During the manufacture of the retainer body 111, at least a portion of the anchor 140a, including the opening 143a, 140a can be positioned inside of an injection mold for the retainer body 111 such that when a polymer is injected to the mold, the polymer material can flow through the opening 143a forming one of the posts 117 to thereby couple the retainer body 111 to the anchor 140a. It should be understood from the description herein that the anchor 140b can also be coupled to the retainer body 111 in a similar overmolding process. It should also be understood that there exist many manufacturing processes that can secure the anchors 140a and 140b to the retainer body 111. In some embodiments, the retainer body 111 and the anchors 140a and 140b can be manufactured as a single piece.

Still referring to FIGS. 5-7, the left portion 101a of the base 110 and the right portion 101b of the base 110 can be formed as a single component that is bendable along the fold line 113. For example, the retainer body 111 can be configured to resiliently maintain the shape depicted in FIG. 5. The base 110 can be transitioned from the deployed configuration depicted in FIGS. 2-3 to the removal configuration depicted in FIG. 7 (e.g., when the user desires to remove the anchor device 20 from a patient). At such time, the user may annually apply a bending moment 102 (FIGS. 7-8) to fold the anchor device 100 along the fold line 113, thus causing the anchor device 100 to transition from the deployed configuration shown in FIGS. 2-3 (where the tines 145a and 145b are substantially oriented in opposing directions) to the removal configuration shown in FIG. 7 (where the tines 145a and 145b are generally adjacent to each other and oriented in substantially the same direction). In the depicted embodiment, the tines 145a and 145b can be rotated about 75-degrees to about 105-degrees, and preferably about 90-degrees, during the transition to the removal configuration.

In some embodiments, the anchor device 100 may be deployed with a corresponding delivery device 150 (described in more detail below in connection with FIGS. 8A-C). In alternative embodiments, the anchor device can be deployed without the need for a corresponding delivery tool. In such circumstances, portions of the anchor device 100 (e.g., the tines 145a and 145b) can be deployed in the subcutaneous region 34 without the use of the delivery tool 150. For example, an IV line can be inserted into a skin penetration point and then secured to in place relative to that penetration point in a similar manner as depicted in FIG. 1. The base 110 can be grasped by a user and maneuvered toward the skin 30. When the tips 142 of the anchors 140a and 140b enter a penetration point, the surrounding skin supplies the force required to flex the tines 145a and 145b against the anchor shafts 141a and 141b. In some embodiments, the anchors 140a and 140b (including the tines 145a and 145b) can comprise a flexible polymer material. The polymer material can be configured to allow the tines 145a and 145b to flex against the anchor shafts 141a and 141b without the use of a deployment tool 150 and to minimize damage to the skin surrounding the penetration point 32.

Figure 8A:
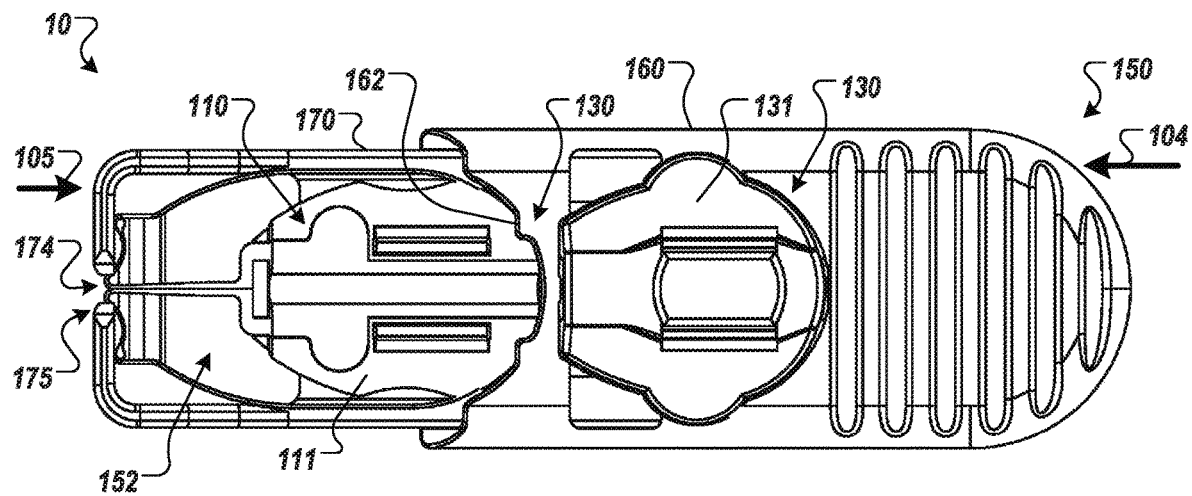
FIGS. 8A-8C depict top, side, and front views of the anchor device of FIG. 1 in a shipping configuration within a delivery tool, in accordance with some embodiments.
Figure 8B:
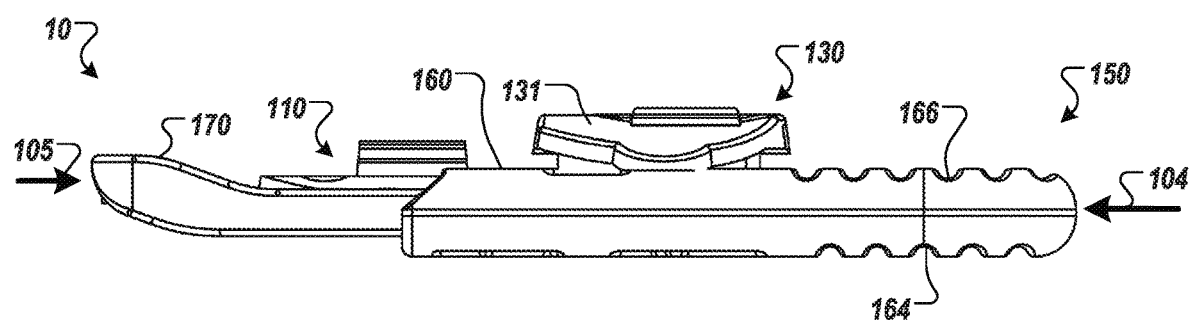
Figure 8C:
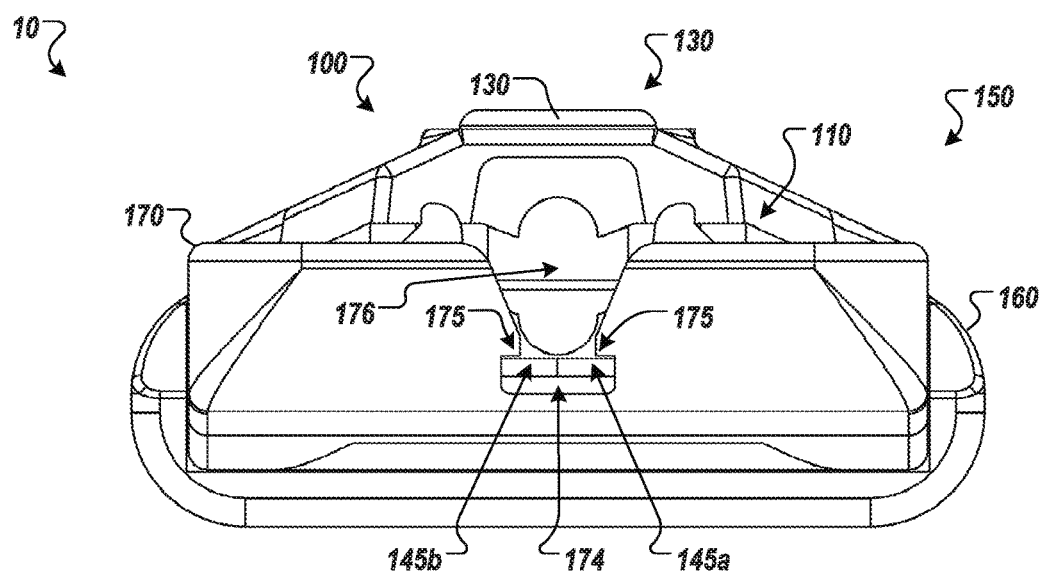

Referring now to FIGS. 8A-8C, in some embodiments, the anchor device 100 and a corresponding delivery tool 150 can be arranged in a shipping configuration as part of a kit.

For example, the base 110 can be located inside an internal cavity 152 of the delivery tool 150 while the cap assembly 130 is separately coupled to the delivery tool 150. The delivery tool 150 can include an outer housing 160 and a device tray 170 that are slidably coupled to each other to define the internal cavity 152. The delivery tool 150 can incorporate features to secure the base 110 and the cap assembly 130 in the kit. For example, the cavity 152 of the delivery tool 150 can secure the base in the package before it is prepared for deployment. Also, the cap assembly 130 can mate with tabs extending from the outer housing 160 of the delivery tool 150. After the tines 140a-b of the base 110 are deployed in the subcutaneous layer 34 of skin, the delivery tool 150 can be decoupled from the base 110. The cap assembly 130 can be separated from the delivery tool 150 (e.g., in a manner similar to the removal of the cap assembly 130 from the base 110 as described in connection with FIG. 4) and later removably coupled to the base 110 (to secure the position of the catheter 20 relative to the base 110). For example, in the shipping configuration depicted in FIGS. 8A-8C, the anchor base 110 can be retained in the internal cavity 152 by a lip 162 of the outer housing 160 and the shape of a distal opening 174 in the device tray 170. In this example, the lip 162 of the outer housing 160 can retain a portion of base 110 by overlapping a portion of the base 110 and restricting the movement of the proximal portion 103 of the anchor device 100. As can be seen in FIGS. 8A and 8C, the distal opening 174 can allow the anchors 140a and 140b to protrude from the device tray 170 while tabs 175 cooperate with the tines 145a and 145b to slidably couple the base 110 to the device tray 170. In some embodiments, a user can grasp the delivery device 150 by placing the index finger on the lower grip 164 and the thumb on the upper grip 166 of the outer housing 160. To insert a portion of the anchor device 100 in the skin 30, the distal opening 174 in the insertion device 150 can be positioned adjacent to the skin penetration point 32.

In some embodiments, the tines 140a-b of the base 110 can deploy from the delivery device 150 by applying a pushing force 104 can to the outer housing 160 (e.g., by a user) while an opposing force 105 (e.g., applied by the skin 30, a user, or a combination thereof) acts on the tray 170. As forces 104 and 105 are applied, the outer housing 160 moves generally in the direction of force 104, relative to the device tray 170. The portion of the outer housing 160 abutting the base 110 can cause the base 110 to move in the direction of the force 104, relative to the device tray 170 and can cause the anchors 140a and 140b to protrude from the distal opening 174. Structures defined by the outer housing 160 and the device tray 170 may retain the base 110 within the cavity 152 until the tines 145a and 145b are fully deployed outside of the cavity 152. While translating within the cavity 152, the base 110 can be retained in the cavity 152 by the cooperation of the lip 162 with the retainer body 111 and the cooperation of the tines 145a and 145b with the tabs 175. When the tines 145a and 145b deploy outside of the cavity 152, the anchors 140a and 140b are free to move out of the cavity 152 (through channel 176), thus releasing the base 110 from the device tray 170. Once free from the device tray 170, the base 110 can move relative to the outer housing 160, thereby releasing from the outer housing 160. When the base 110 is decoupled from the housing 160 and the tray 170, the delivery device 150 can be removed, allowing the base 110 to remain in place (e.g., with the anchors 140a-b in the subcutaneous layer 34 of skin). The cap assembly 130 can be lifted from the delivery tool 150 and coupled to the base 110 to secure the catheter 20, for example, in a selected position relative to a patient's skin.

Referring now to FIGS. 9-15, in use, the anchor device 100 can be used to retain a medical instrument 20, such as a catheter, in an operative position relative to a skin incision. As previously described, the anchor device 100 and the delivery tool 150 can include features to facilitate the deployment of at least a portion of the anchor device 100 in the subcutaneous layer 34 of a patient. In some embodiments, the skin penetration point 32 can be surgically opened in the skin 30 so that the catheter 20 can be inserted through the penetration point 32, through the subcutaneous region 34, and into a targeted vein 40 or other bodily lumen. After the catheter 20 is inserted, the anchor device 100 can be deployed to secure the catheter 20 relative to the penetration point 32.

Figure 9:
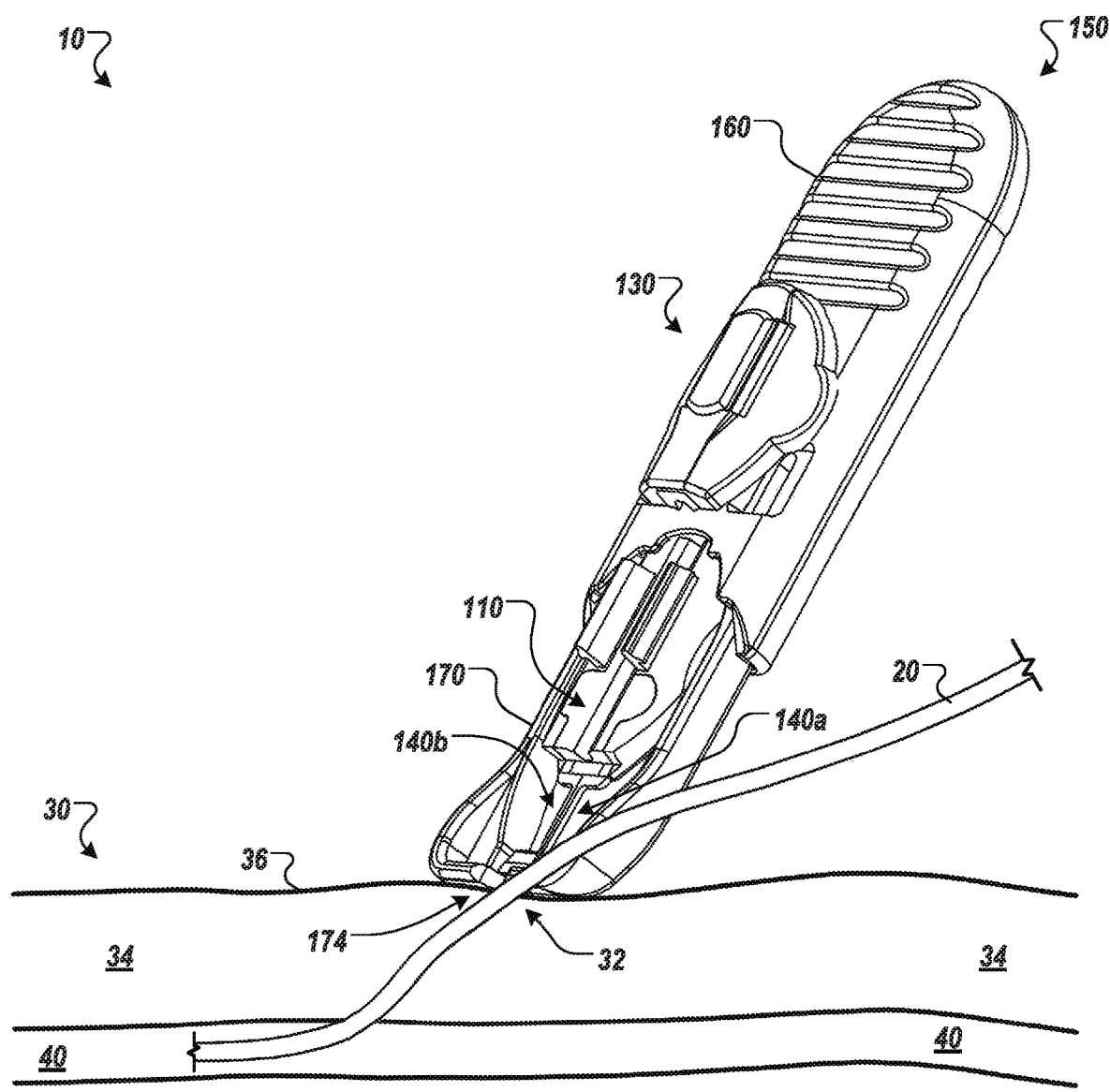
FIGS. 9-15 are perspective views of an anchor system, including the anchor device of FIG. 1, for use in securing the position of a medical instrument.

Referring now to FIG. 9, the anchor system 10 (e.g., including the anchor device 100 and the delivery device 150 depicted in FIGS. 8A-8C) can be guided until the distal opening 174 of the delivery device 150 is adjacent to the skin penetration point 32 that is occupied by the catheter 20. Once in this location, the user can apply a pushing force (refer to force 104 in FIGS. 8A-B) to the outer housing 160 with an opposing force (refer to force 105 in FIGS. 8A-B) away from the skin 30 applied by the skin 30 against the front face 156 of the insertion device 150 to deploy the tines 145a-b of the base 110. During this application of the pushing force, the outer housing 160 can move toward the skin 30 while the front face remains substantially abutting the skin 30 adjacent to the skin penetration point 32.

Referring now to FIG. 10, as the outer housing 170 moves relative to the device tray 160 toward the skin 30, the base 110 can translate within the cavity 152 and the tips 142 of the anchors 140a and 140b can exit through the opening 174 in the front face of the delivery device 150 and into the skin penetration point 32 (e.g., through the same incision through which the catheter 20 was previously inserted). As the anchors 140a and 140b exit the insertion device 150, the tines 145a and 145b may flex against the shafts 141 and 141b of the anchors 140a and 140b due to the force applied by the sides of the opening 174. By resiliently flexing against the anchor shafts 141a and 141b, the tines 145a and 145b can pass through the penetration point 32 in a way that reduces the likelihood of damage to the tissue surrounding the penetration point 32. As the anchors 140a and 140b exit the insertion device 150 through the opening 174, the tines 145a and 145b can advance into the subcutaneous layer 34. The tines 145a and 145b can be biased to return toward the deployed configuration, as previously described in connection with FIGS. 2-3.

Figure 11:
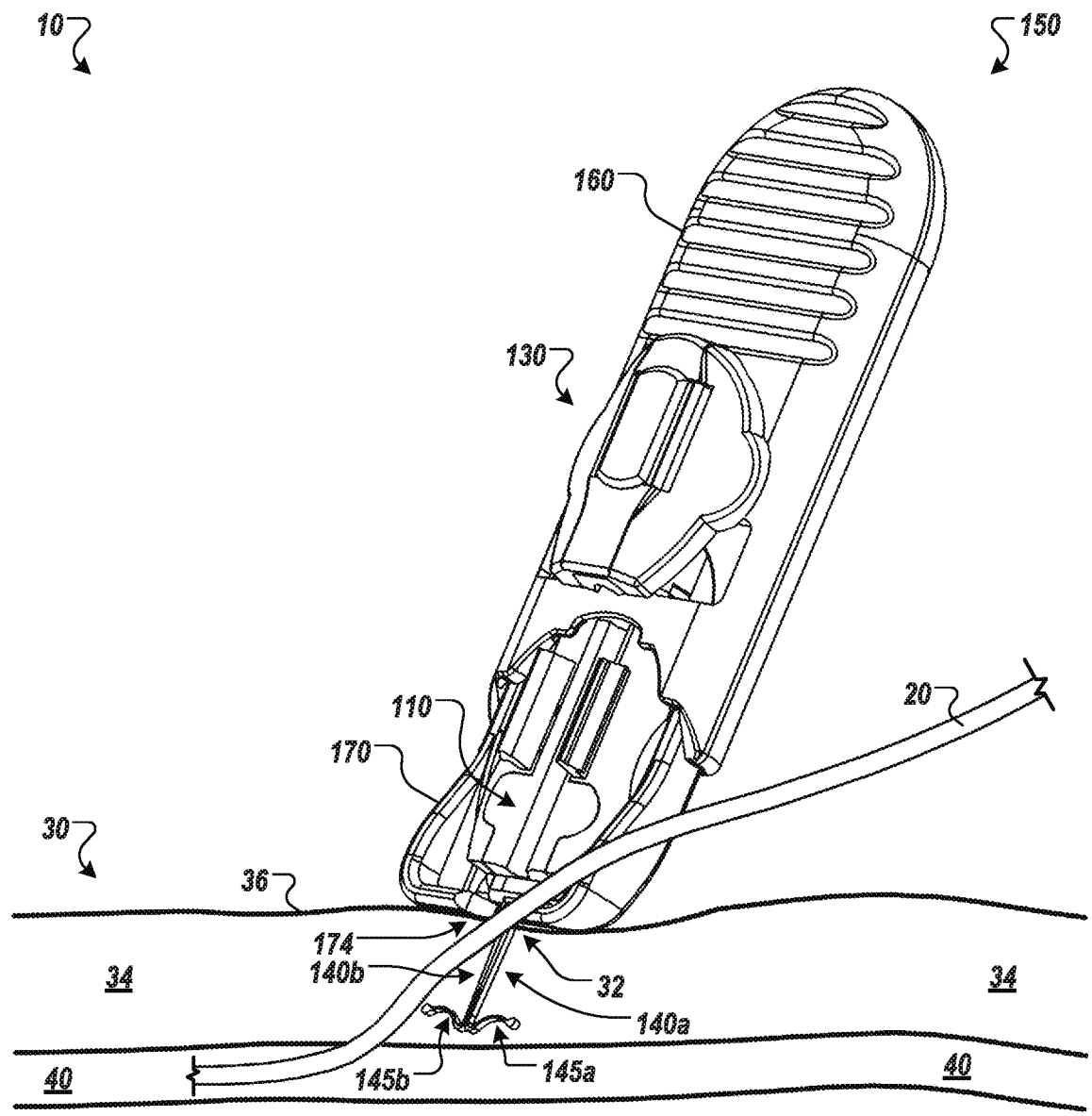

Referring now to FIG. 11, after the anchors 140a and 140b penetrate the skin 30 so that the tines 145a and 145b pass into the subcutaneous region 34, the tines 145a and 145b can resiliently return toward the deployed configuration in which the first tine 145a extends outwardly away from the second tine 145b. The curved shape of the tines 145a and 145b can allow them to deploy adjacent to and abut the underside of the skin 30 to anchor the device 100 relative to the skin without tearing the dermal layers 36. As described previously in connection with FIGS. 8A-8C, once the tines 145a and 145b have deployed from the delivery tool 150, the deployment device 110 can become decoupled from the delivery tool 150.

Figure 12:
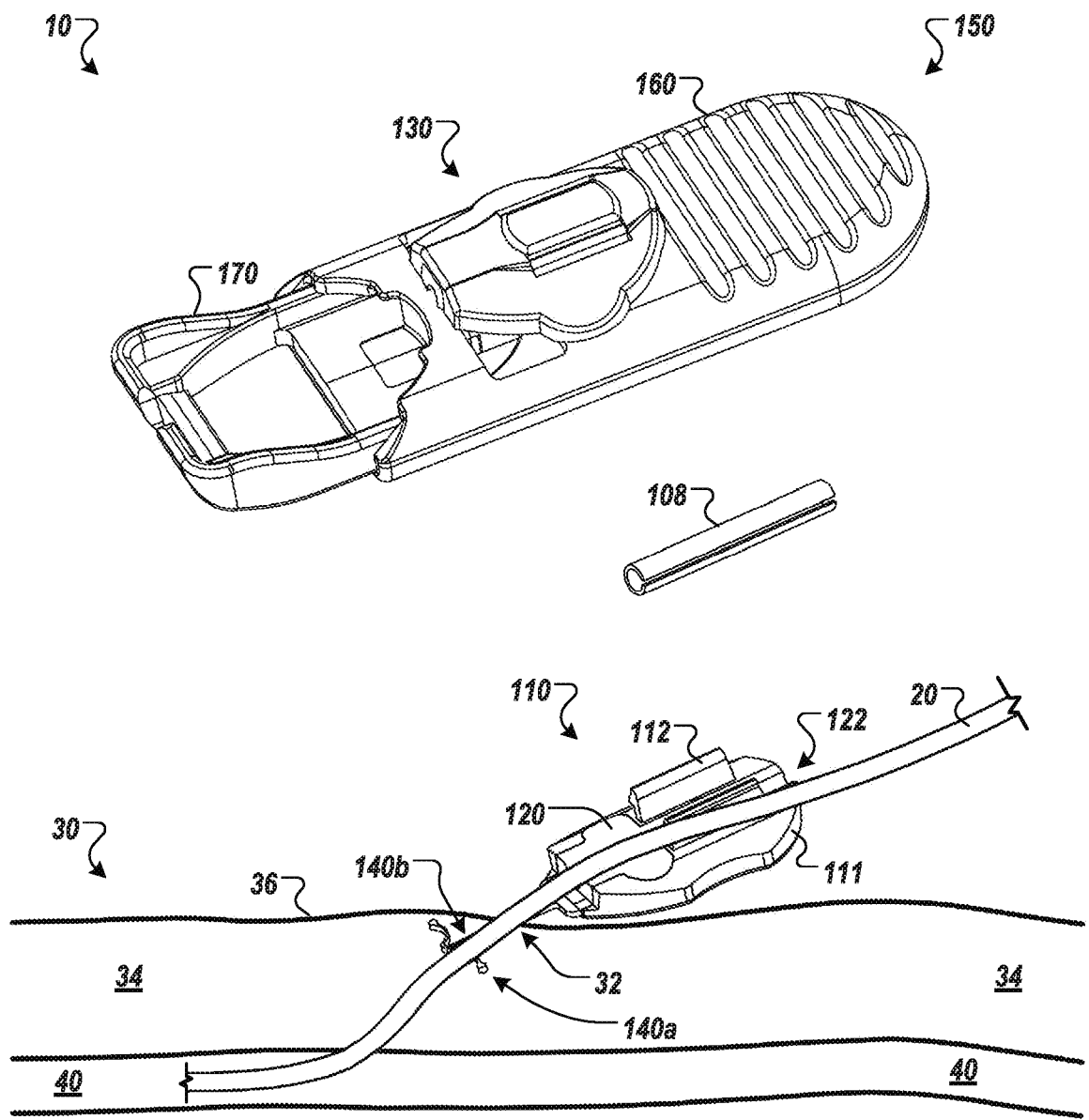
Figure 13:
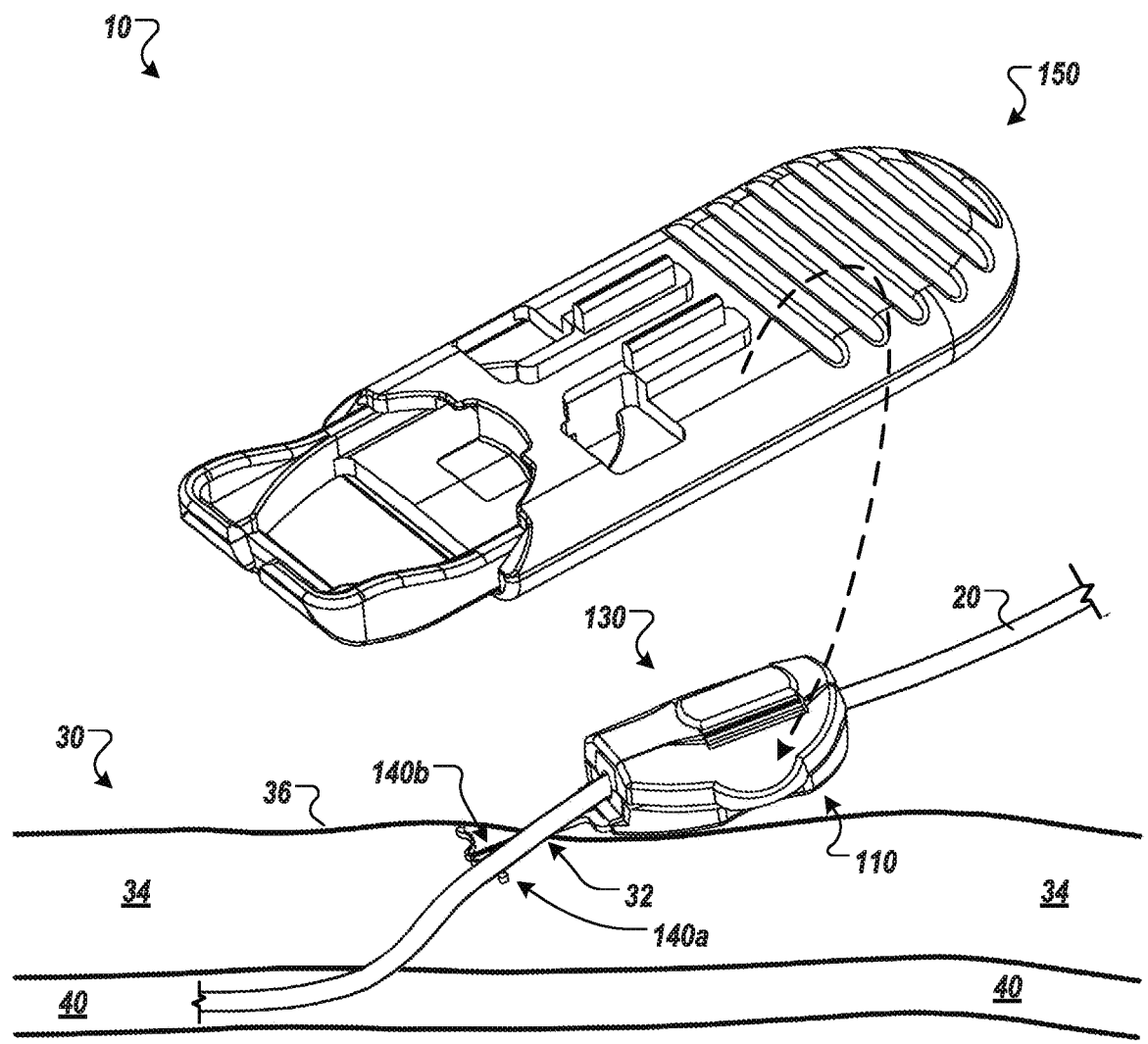

Referring now to FIGS. 12-13, to retain the catheter 20 in an operative position, the catheter can be positioned along the channel 122 of the retainer portion 120. The user can decouple the cap assembly 130 from the delivery tool 150 and press the cap assembly 130 to the base 110 to compress the retainer portions 120 and 135 onto the outer surface of the catheter 20 (to provide a frictional holding force thereon), thus transitioning the anchor device 100 to the closed configuration. To reposition the catheter 20, the cap assembly 130 can be separated from the base 110 by applying pressure to the locking tabs 112 to move the tips 115 closer to each other until the cap assembly 130 is separated from the base 110, thus transitioning the anchor device 100 to the open configuration (refer to FIGS. 2-3). As the catheter 20 is no longer secured in place by the anchor device 100, it can be repositioned (advanced distally or withdrawn proximally) before being secured once again to the anchor device 100 by coupling the cap assembly 130 to the base 110. Optionally, a flexible sleeve 108 can be fit over the catheter 20 if the outer diameter of the catheter 20 is too small to releasably secure inside the channel 122 of the retainer portion 120. The flexible sleeve 108 may comprise a silicone material or another polymer material so that a compression force applied to the sleeve 108 creates a friction holding force upon the catheter 20. The sleeve 108 may be provide as part of the kit described in connection with FIGS. 8A-C and may be releasably secured to the delivery device 150 during shipment.

Figure 14:
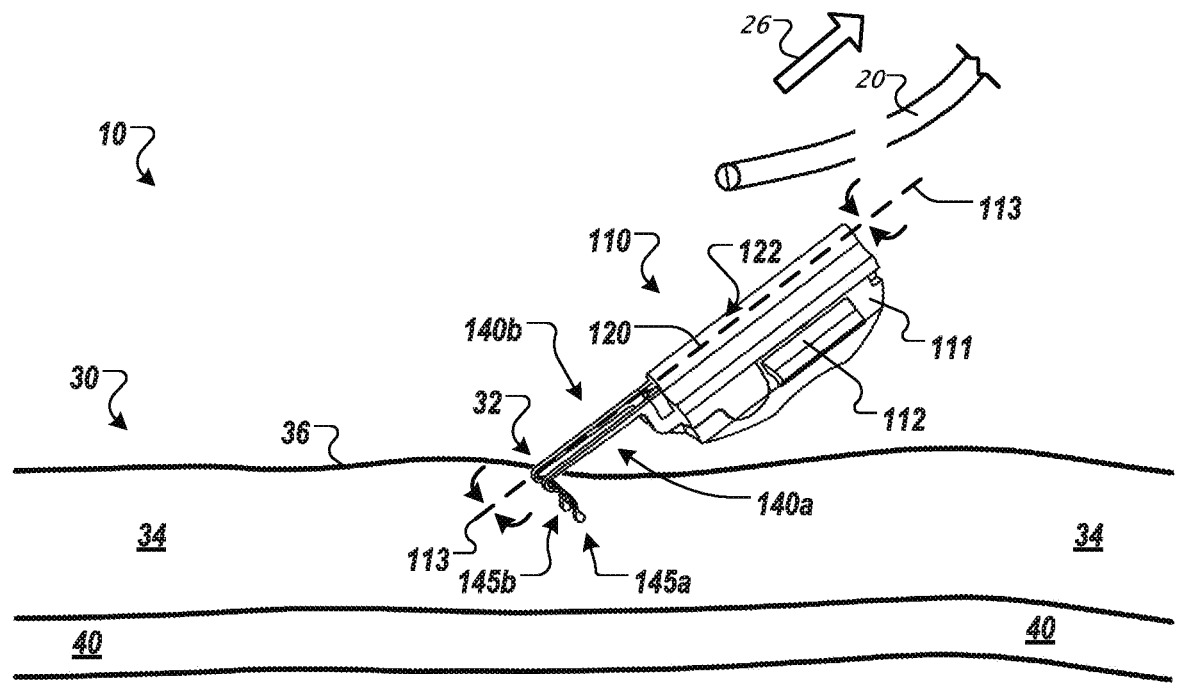

Referring now to FIG. 14, when the catheter 20 is ready to be withdrawn from the patient, the catheter 20 can be withdrawn from the patient separately from the anchor device 100. In one example, after a catheter procedure is complete, the cap assembly 130 can be separated from the base 110, thus allowing the catheter 20 to be lifted away from the channel 122 of the flexible portion 120. After the catheter 20 is dissociated from the anchor device 100, the catheter 20 can be removed from the skin 30 by application of a withdrawal force 26 (while the base 110 remains coupled to the skin 30).

As previously described, the left portion 101a of the anchor device 100 can be pivoted with respect to the right portion 101b before removing the anchors 140a and 140b from the subcutaneous region 34 under the skin 30. In some embodiments, the left retainer body portion 114a and the right retainer body portion 114b are manufactured as an integral piece with a flexible fold line 113 (along a central longitudinal axis in this embodiment). As such, the body portions 114a and 114b can be pivoted with respect to each other while the anchor tines 145a and 145b are deployed in the subcutaneous region 34 (refer to FIG. 14). Accordingly, the anchors 140a and 140b (including the tines 145a and 145b) can collectively penetrate into the subcutaneous region 34 in a configuration depicted in FIG. 11, and may be pivoted into the removal configuration shown in FIG. 14 for withdrawn from skin penetration point 32. In some embodiments, two portions 101a and 101b of the base 110 can be pivoted to the removal configuration so as to reduce the likelihood of trauma to the skin 30 surrounding the penetration point 32 during removal of the anchors 140a and 140b. In some circumstances, the folded anchor device 100 can be maneuvered as to reduce the cross sectional area of the portion of the anchors 140a and 140b being withdrawn through the dermal layers 36, thus reducing the likelihood of damaging the surround skin tissue during removal of the anchors 140a and 140b (refer to FIG. 14).

Figure 15:
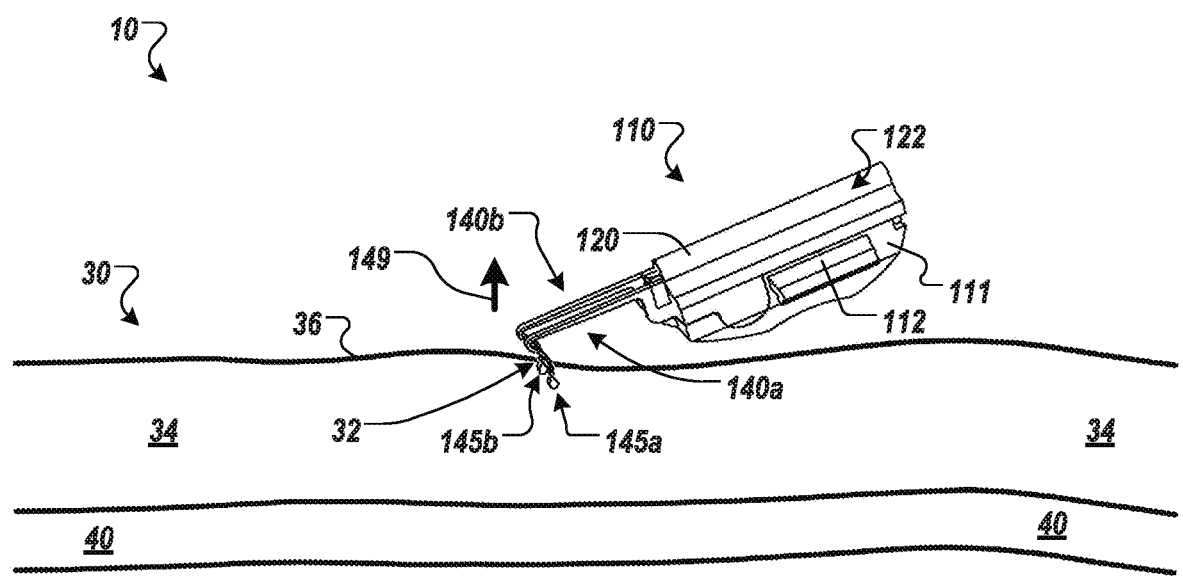

Referring now to FIG. 15, the anchor device 100 can be removed from the patient's skin 30 in a manner that contemporaneously withdraws the anchor tines 145a and 145b in a generally side-by-side arrangement. As described previously in connection with FIG. 14, the anchor device 100 can be folded such that the anchors 140a and 140b are adjacent to each other and oriented in substantially the same direction (e.g., the tips 146 of the tines 145a and 145b may be shifted proximate to one another). The anchor device 100 can be maneuvered to simultaneously remove the anchors 140a and 140b from the skin 30. For example, when the tines 145a and 145b are pivoted to the side-by-side arrangement, the user may apply an upward force 149 that lifts the anchors 140a and 140b away from the skin (with the tips 146 of the tines 145a and 145b being at the trailing end). Such a removal process can be used to reduce the cross sectional area of the portion of the anchors 140a and 140b being withdrawn through the dermal layers 36, thereby reducing the likelihood of damaging the surrounding skin tissue during removal of the anchors 140a and 140b. It should be understood from the description herein that, in some embodiments, the anchor device 100 can be removed from the skin 30 (e.g., in a manner similar to that depicted in FIGS. 14-15) while the catheter 20 remains in the skin 30.

A number of embodiments of the invention have been described. Nevertheless, it will be understood that various modifications may be made without departing from the spirit and scope of the invention. Accordingly, other embodiments are within the scope of the following claims.

What is claimed is:

1. An anchor system for securing the position of a medical device relative to a patient skin opening, comprising:
    an anchor device configured to releasably secure to an external portion of a medical device while another portion of the medical device occupies a skin opening, the anchor device including:
    a retainer base comprising a flexible hinge region, and
    one or more subcutaneous anchors positioned distally from a distal end of the retainer base to anchor in the skin opening, each anchor comprising: a longitudinal shaft portion that extends in a distal direction to a position that is distal of the distal end of the retainer base, and a flexible tine that deploys in a subcutaneous region to secure the retainer base relative to the skin opening,
    wherein each flexible tine of said one or more subcutaneous anchors is pivotable along the flexible hinge region so as to adjust said one or more subcutaneous anchors from a deployed configuration to a removal configuration, wherein a first body portion of the retainer base is pivotable about a pivot axis defined by the flexible hinge region relative to a second body portion of the retainer base while the first and second body portions remain physically coupled to one another, and said one or more subcutaneous anchors comprise a first anchor coupled to the first body portion and a second anchor coupled to the second body portion and wherein the first body portion and the second body portion of the retainer base are formed as a single component that is bendable along the pivot axis so as to pivot the first body portion relative to the second body portion; and
    a delivery device that defines an internal space and a distal opening, the retainer base positionable within the internal space and separable from the delivery device when the delivery device deploys the one or more subcutaneous anchors from the distal opening.

2. The anchor system of claim 1, wherein the flexible hinge region includes an upwardly facing channel to frictionally engage with the external portion of the catheter.

3. The anchor system of claim 2, wherein each flexible tine of said one or more subcutaneous anchors is pivotable along the flexible hinge region about a pivot axis that extends below the upwardly facing channel of the flexible hinge region.

4. The anchor system of claim 1, wherein the anchor device is deployable from the internal space of the delivery device.

5. The anchor system of claim 4, wherein the internal space is at least partially defined by an outer housing and a device tray slidably coupled to the outer housing.

6. The anchor system of claim 1, wherein the delivery device is configured to retain the tines in a flexed condition in which the tines are flexed against respective shafts while the anchor device is deployed from the internal space.

7. The anchor system of claim 6, wherein the tines shift to a deployed configuration in which the tines extend outwardly from the respective shafts after the tines are deployed from the internal space into the skin opening.

8. The anchor system of claim 1, wherein said one or more subcutaneous anchors comprise a metallic material that exhibits superelasticity when used in a human body.

9. The anchor system of claim 1, further comprising a flexible sleeve to fit over an outer circumferential surface of the external portion of medical device when the retainer base releasably secures with the medical device.

10. The anchor system of claim 1, wherein each of the subcutaneous anchors extends distally forward from the distal end of the retainer base in an amount sufficient to be insertable through the same skin opening occupied by the catheter when the retainer body releasably secures to the catheter.

11. The anchor system of claim 1, wherein each of the subcutaneous anchors comprises the longitudinal shaft portion and the flexible tine which extends outwardly away from the pivot axis toward a free end, and the free end of each anchor comprises a rounded dull tip.

12. An anchor system for securing the position of a medical device relative to a patient skin opening, comprising:
an anchor device configured to releasably secure to an external portion of a medical device while another portion of the medical device occupies a skin opening, the anchor device including:
a retainer base comprising a flexible hinge region,
one or more subcutaneous anchors positioned distally from a distal end of the retainer base to anchor in the skin opening, each anchor comprising: a longitudinal shaft portion that extends in a distal direction to a position that is distal of the distal end of the retainer base, and a flexible tine that deploys in a subcutaneous region to secure the retainer base relative to the skin opening, and
a cap releasably mountable to the retainer body so as to define a covered channel between the cap and a upwardly facing channel of the retainer body for engagement with the external portion of the medical device,
wherein each flexible tine of said one or more subcutaneous anchors is pivotable so as to adjust said one or more subcutaneous anchors from a deployed configuration to a removal configuration; and
a delivery device that defines an internal space and a distal opening, the retainer base positionable within the internal space and separable from the delivery device when the delivery device deploys the one or more subcutaneous anchors from the distal opening;
wherein a first body portion of the retainer base is pivotable about a pivot axis defined by the flexible hinge region relative to a second body portion of the retainer base while the first and second body portions remain physically coupled to one another, and said one or more subcutaneous anchors comprise a first anchor coupled to the first body portion and a second anchor coupled to the second body portion.

13. The anchor system of claim 12, wherein the anchor device is deployable from the internal space of the delivery device.

14. The anchor system of claim 13, wherein the internal space is at least partially defined by an outer housing and a device tray slidably coupled to the outer housing.

15. The anchor system of claim 14, wherein the delivery device is configured to retain the tines in a flexed condition in which the tines are flexed against respective shafts while the anchor device is deployed from the internal space.

16. The anchor system of claim 15, wherein the tines shift to a deployed configuration in which the tines extend outwardly from the respective shafts after the tines are deployed from the internal space into the skin opening.

17. The anchor system of claim 12, wherein each of the one or more subcutaneous anchors extends distally of a distalmost face of the retainer base so as to be positioned to insert through the same skin opening as the catheter when the retainer body releasably secures to the catheter.

* * * * *